United States Patent
Petersen et al.

(10) Patent No.: US 7,390,913 B2
(45) Date of Patent: *Jun. 24, 2008

(54) PROCESS FOR THE PREPARATION OF RACEMIC CITALOPRAM DIOL AND/OR S- OR R-CITALOPRAM DIOLS AND THE USE OF SUCH DIOLS FOR THE PREPARATION OF RACEMIC CITALOPRAM, R-CITALOPRAM AND/OR S-CITALOPRAM

(75) Inventors: Hans Petersen, Vanløse (DK); Brian Christiansen, Frederiksberg (DK); Robert Dancer, Hvidovre (DK); Rikke E. Humble, Copenhagen (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 353 days.

This patent is subject to a terminal disclaimer.

(21) Appl. No.: 10/540,300

(22) PCT Filed: Dec. 18, 2003

(86) PCT No.: PCT/DK03/00907

§ 371 (c)(1),
(2), (4) Date: Jul. 14, 2005

(87) PCT Pub. No.: WO2004/056754

PCT Pub. Date: Jul. 8, 2004

(65) Prior Publication Data

US 2006/0020140 A1    Jan. 26, 2006

Related U.S. Application Data

(60) Provisional application No. 60/436,117, filed on Dec. 23, 2002.

(30) Foreign Application Priority Data

Dec. 23, 2002    (DK) ................................ 2002 02004

(51) Int. Cl.
    C07D 307/78    (2006.01)
    C07D 307/87    (2006.01)
    C07D 307/93    (2006.01)
(52) U.S. Cl. .......................... 549/476; 549/469; 549/471
(58) Field of Classification Search ................. 549/476, 549/469, 471
See application file for complete search history.

(56) References Cited

FOREIGN PATENT DOCUMENTS

EP          0 347-066 A1    12/1989
WO    WO-03/000672 A1       1/2003

*Primary Examiner*—D. Margaret Seaman
*Assistant Examiner*—Nizal S Chandrakumar
(74) *Attorney, Agent, or Firm*—Darby & Darby P.C.

(57) ABSTRACT

In the following, citalopram diol means 4-(4-(dimethylamino)-1-(4-fluorophenyl)-1-hydroxybutyl)-3-(hydroxymethyl)-benzonitrile, as free base and/or acid addition salt. The invention relates to a process for the preparation of racemic citalopram diol and/or R- or S-citalopram diol, comprising the separation of a non-racemic mixture of R- and S-citalopram diol with more than 50% of one of the enantiomers into a fraction being enriched with S- or R-citalopram diol and a fraction comprising RS-citalopram diol wherein the ratio of R-citalopram diol:S-citalopram diol is equal to 1:1 or closer to 1:1 than in the initial mixture. The method is characterized in that (i) RS-citalopram diol is precipitated from a solution of the initial non-racemic mixture, or R- or S-citalopram diol is dissolved into a solvent from the initial non-racemic mixture, leaving a residue of RS-citalopram diol, and in that (ii) the residue/precipitate formed is separated from the final solution phase, followed by optional steps of repetition, recrystallisation, purification, isolation and conversion between free base and salts. The invention also relates to a process for the preparation of RS-citalopram, S-citalopram or R-citalopram (all as free base and/or acid addition salt) comprising the method described above followed by ring closure.

42 Claims, No Drawings

PROCESS FOR THE PREPARATION OF RACEMIC CITALOPRAM DIOL AND/OR S- OR R-CITALOPRAM DIOLS AND THE USE OF SUCH DIOLS FOR THE PREPARATION OF RACEMIC CITALOPRAM, R-CITALOPRAM AND/OR S-CITALOPRAM

This application is a §371 national stage of International Application No. PCT/DK03/00907, filed Dec. 18, 2003, which was published in English as International Publication No. WO 2004/056754, and claims the benefit of U.S. Provisional Application No. 60/436,117, filed Dec. 23, 2002.

The invention relates to a process for the preparation of racemic citalopram diol and R- or S-citalopram diol by separating an initial non-racemic mixture of the compounds R- and S-citalopram diol (R- and S-4-[4-(dimethylamino)-1-(4'-fluorophenyl)-1-hydroxybutyl]-3-(hydroxymethyl)-benzonitrile) into a fraction of racemic citalopram diol and a fraction being enriched with S-diol or R-diol. The invention also relates to the use of such isolated citalopram diols for the formation of the corresponding racemic citalopram and/or S- or R-citalopram to be comprised in a pharmaceutical composition.

BACKGROUND OF THE INVENTION

Citalopram is a well-known antidepressant drug that has now been on the market for some years and has the following structure:

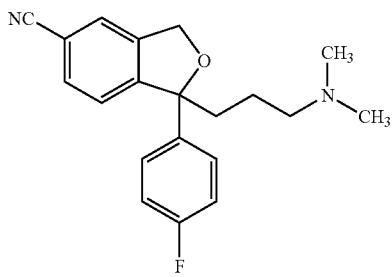

Citalopram may be prepared by ring closure of 4-[4-(dimethylamino)-1-(4'-fluorophenyl)-1-hydroxybutyl]-3-(hydroxymethyl)-benzonitrile (racemic citalopram diol) as described in U.S. Pat. No. 4,650,884. The product citalopram is a racemic mixture of the R- and S-enantiomers.

Further, the S-enantiomer of citalopram (escitalopram) is a valuable antidepressant of the selective serotonin reuptake inhibitor (SSRI) type. Escitalopram may be prepared by ring closure of S-4-[4-(dimethylamino)-1-(4'-fluorophenyl)-1-hydroxybutyl]-3-(hydroxymethyl)-benzonitrile (S-diol) with retention of configuration as described in EP B1 347 066. The amount of R-citalopram compared to S-citalopram in the product escitalopram should be less than 3%.

Furthermore, a method for the preparation of a mixture of R- and S-citalopram with more than 50% of the S-enatiomer from a mixture of R- and S-diol with more than 50% of the R-diol is described in WO03000672.

It appears from the above, that products of racemic citalopram and escitalopram with the above-mentioned enantiomeric purity are required for the preparation of pharmaceutical compositions and that racemic citalopram and escitalopram products may be prepared by ring closure of the RS-diol and R-diol and/or S-diol. As a consequence, methods for the preparation of products of racemic diol and S-diol being correspondingly enantiomerically pure are required.

Processes for the preparation and purification of R- or S-diol products are available. Such processes involve for instance enantio-selective synthesis as described in EP 0347066, classical resolution and chromatographic separation as described in WO03006449. Depending on the specific process and the conditions used, the enantiomeric purity of the S-diol product may have to be improved before the S-diol product will meet the above requirements.

Surprisingly, it has now been found that by using the process of the invention an expensive, but apparently useless S-diol product being contaminated with R-diol, may easily be converted into the two valuable products, racemic diol and S-diol, which meet the above requirements as regards enantiomeric purity.

Furthermore, by using the process of the invention, an expensive, but apparently useless R-diol product being contaminated with S-diol, may easily be converted into the valuable products, racemic diol and R-diol, which meet the above requirements as regards enantiomeric purity.

More particularly, the present invention provides a process for the separation of an initial non-racemic mixture of R- and S-4-[4-(dimethylamino)-1-(4'-fluorophenyl)-1-hydroxybutyl]-3-(hydroxymethyl)-benzonitrile with more than 50% of one of the enantiomers into a fraction being enriched with S-diol or R-diol and a fraction comprising RS-diol, wherein the ratio of R-diol:S-diol is equal to 1:1 or closer to 1:1 than in the initial mixture of R- and S-diol.

The process of the invention is important and very useful, in particular because it provides a convenient, cheap and efficient way to transform a mixture of R- and S-diols which does not meet the above requirements as regards enantiomeric purity into two valuable products, RS-diol and S-diol (or R-diol), which meet the above requirements as regards enantiomeric purity.

In another aspect, the invention provides a convenient, cheap and efficient method for making an intermediate to be used in the manufacturing of citalopram and escitalopram.

With the present invention, the process for the production of racemic citalopram and escitalopram meeting the requirements of the respective marketing approvals has become more rational and more economical as regards the simplicity of the process and the utilisation of reagents and resources.

SUMMARY OF THE INVENTION

Thus, the present invention relates to a process for the preparation of racemic diol free base and/or acid addition salt and/or R- or S-diol free base and/or an acid addition salt comprising a separation of an initial non-racemic mixture of R- and S-diol free base and/or acid addition salt with more than 50% of one of the enantiomers into a fraction being enriched with S-diol or R-diol free base and/or acid addition salt and a fraction comprising RS-diol free base and/or acid addition salt wherein the ratio of R-diol:S-diol is equal to 1:1 or closer to 1:1 than in the initial mixture of R- and S-diol wherein i) RS-diol free base and/or acid addition salt is precipitated from a solution of the initial non-racemic mixture of R- and S-diol free base and/or acid addition salt; or R- or S-diol free base and/or acid addition salt is dissolved into a solvent from the initial non-racemic mixture of R- and S-diol free base and/or acid addition salt in said solvent, leaving a residue comprising RS-diol free base and/or acid addition salt;

ii) the residue/precipitate formed is separated from the final solution phase;

iia) if the residue/precipitate is crystalline it is optionally recrystallised one or more times to form racemic diol;

iib) if the residue/precipitate is not crystalline, steps i) and ii) are optionally repeated until a crystalline residue/precipitate is obtained and the crystalline residue/precipitate is optionally recrystallised one or more times to form racemic diol;

iii) the final solution phase is optionally subjected to further purification and S-diol or R-diol free base and/or acid addition salt is isolated from the final solution phase;

iv) the free bases of the diols obtained are optionally converted to acid addition salts thereof or acid addition salts of the diols obtained are optionally converted to other acid addition salts or acid addition salts of the diols obtained are optionally converted to the corresponding free bases.

Accordingly, the RS-diol free base and/or acid addition salt obtained gives rise to the final solution phase being enriched with either the S- or R-diol free base and/or acid addition salt. The surplus of R- or S-diol free base and/or acid addition salt may then be isolated from the final solution phase as described below.

According to a specific embodiment, the invention relates to a process for the preparation of racemic diol free base and/or acid addition salt using the process described above.

According to another specific embodiment, the invention relates to a process for the preparation of S-diol (or R-diol) free base and/or an acid addition salt using the process described above.

According to still another specific embodiment, the invention relates to the use of the prepared racemic diol free base and/or acid addition salt and/or S-diol (or R-diol) free base and/or an acid addition salt for the preparation of racemic citalopram and/or S-citalopram (or R-citalopram) free base and/or acid addition salt using the process described below.

DETAILED DESCRIPTION OF THE INVENTION

Whenever used in this document, the terms "S-diol" and "S-citalopram diol" mean S-4-[4-(dimethylamino)-1-(4-fluorophenyl)-1-hydroxybutyl]-3-(hydroxymethyl) benzonitrile.

Whenever used in this document, the terms "R-diol" and "R-citalopram diol" mean R-4-[4-(dimethylamino)-1-(4-fluorophenyl)-1-hydroxybutyl]-3-(hydroxymethyl) benzonitrile.

Whenever used in this document, the term "RS-diol" means a mixture of R- and S-diol such as a 0.5:1.5 or 0.9:1.1 or 0.95:1.05 or 0.98:1.02 or 0.99:1.01 mixture of R- and S-diol and preferably a mixture with a 1:1 ratio of the R- and S-diol.

Whenever used in this document, the terms "diol enantiomer" and "diol isomer" mean either S- or R-diol.

Whenever used in this document, the term "racemic diol" means a 1:1 mixture of the R- and S-diols. The term "non-racemic mixtures of diols" means mixtures which contain R- and S-diols in a ratio other than 1:1.

Whenever used in this document, the terms "citalopram enantiomer" and "citalopram isomer" mean either S- or R-citalopram.

Whenever used in this document, the term "racemic citalopram" means a 1:1 mixture of R- and S-citalopram. The term "non-racemic citalopram" means mixtures which contain R- and S-citalopram in a ratio other than 1:1.

As used in this description, the term "precipitation" means forming a precipitate, in the form of crystals, an amorphous solid or an oil or mixtures thereof, from a solution of the initial non-racemic mixture of R- and S-diol in a solvent. In the present description, a precipitate may be an oil, an amorphous solid or crystals or mixtures thereof.

As used in this description, the term "residue" refers to the residue remaining after dissolving R- or S-diol into a solvent from an initial non-racemic mixture of R- or S-diols. The residue may be in the form of crystals, an amorphous solid or an oil or mixtures thereof.

As used herein, the term "residue/precipitate" refers to either a precipitate or a residue as defined above.

As used herein, the term "mother liquor" means the solvent remaining after removal or separation from the precipitate.

As used herein, the term "organic and/or aqueous phase resulting from the selective dissolution of R- or S-diol" refers to the phase wherein R- or S-diol is dissolved from an initial non-racemic mixture of R- or S-diols.

As used herein, the term "final solution phase" refers to a mother liquor or an organic and/or aqueous phase resulting from the selective dissolution of R- or S-diol as defined above.

As already mentioned, the above processes for the preparation of citalopram free base and/or acid addition salt and/or escitalopram free base and/or acid addition salt may result in a mixture of R- and S-citalopram free base and/or acid addition salt which is not acceptable for pharmaceutical use. According to the present invention, a surprisingly efficient process for the preparation of racemic diol and R- or S-diol free base and/or acid addition salt to be used for the preparation of racemic citalopram free base and/or acid addition salt and R- or S-citalopram free base and/or acid addition salt has been found.

This new process involves the separation of an initial non-racemic mixture of R- and S-diol free base and/or acid addition salt into a fraction of racemic diol free base and/or acid addition salt and a fraction of R- or S-diol free base and/or acid addition salt. The fraction of racemic diol free base and/or acid addition salt is precipitated as an oil, an amorphous solid or in crystalline form or mixtures thereof from a solvent, and the R- or S-diol free base and/or acid addition salt is isolated from the final solution phase. Then, racemic citalopram free base and/or acid addition salt and R- or S-citalopram free base and/or acid addition salt may be formed from the corresponding racemic diol free base and/or acid addition salt and R- or S-diol free base and/or acid addition salt by ring closure.

According to another aspect of the invention, the initial non-racemic mixture of R- and S-diol free base and/or acid addition salt is separated into a fraction being enriched with S-diol or R-diol free base and/or acid addition salt and a fraction comprising RS-diol free base and/or acid addition salt wherein the ratio of R-diol:S-diol is equal to 1:1 or closer to 1:1 than in the initial mixture of R- and S-diol by mixing the initial non-racemic mixture of R- and S-diol free base and/or acid addition salt with a solvent and allowing preferentially the R- or S-diol free base and/or acid addition salt to dissolve in the solvent followed by separation of the undissolved RS-diol free base and/or acid addition salt residue from the organic and/or aqueous phase resulting from the selective dissolution of R- or S-diol free base and/or acid addition salt and isolation of R- and S-diol free base and/or acid addition salt from said solvent.

The solvent used according to this embodiment of the invention is any solvent which allow preferentially the R- or S-diol free base and/or acid addition salt to dissolve leaving a mixture of RS-diol free base and/or an acid addition salt wherein the ratio of R-diol:S-diol is equal to 1:1 or closer to 1:1 than in the initial mixture of R- and S-diol as a residue. Useful solvents are solvents such as those mentioned for the precipitation of RS-diol free base and/or RS-diol acid addition salts.

The initial non-racemic mixture of R- and S- diol free base and/or acid addition salt used in the process of the invention may be an oil, an amorphous solid or in crystalline form; or mixtures thereof.

The residue/precipitate formed in step i) may be an oil, an amorphous solid or in crystalline form; or a mixture thereof. The residue/precipitate formed in step i) is preferably in crystalline form.

According to one embodiment of the invention, the initial non-racemic mixture of R- and S-diol free base and/or acid addition salt used in the process of the invention contains more than 50% of S-diol, or more preferred more than 70% of S-diol or most preferred more than 90% of S-diol.

According to another embodiment of the invention, the initial non-racemic mixture of R- and S-diol free base and/or acid addition salt used in the process of the invention contains less than 99.9% of S-diol, such as less than 99.5% of S-diol, or less than 99% S-diol, or less than 98% of S-diol.

Accordingly, the initial non-racemic mixture of R- and S-diol free base and/or acid addition salt may contain 50%-98% of S-diol, or 50%-99% of S-diol, or 50%-99.5% of S-diol, or 50%-99.9% of S-diol, or 70%-98% of S-diol, or 70%-99% of S-diol, or 70%-99.5% of S-diol, or 70%-99.9% of S-diol, or 90%-98% of S-diol, or 90%-99% of S-diol, or 90%-99.5% of S-diol, or 90%-99.9% of S-diol.

According to another embodiment of the invention, the initial non-racemic mixture of R- and S-diol free base and/or acid addition salt used in the process of the invention contains more than 50% of R-diol, or more preferred more than 70% of R-iol or most preferred more than 90% of R-diol.

According to yet another embodiment of the invention, the initial non-racemic mixture of R- and S-diol free base and/or acid addition salt used in the process of the invention contains less than 99.9% of R-diol, such as less than 99.5% of R-diol, or less than 99% R-diol, or less than 98% of R-diol.

Accordingly, the initial non-racemic mixture of R- and S-diol free base and/or acid addition salt may contain 50%-98% of R-diol, or 50%-99% of R-diol, or 50%-99.5% of R-diol, or 50%-99.9% of R-diol, or 70%-98% of R-diol, or 70%-99% of R-diol, or 70%-99.5% of R-diol, or 70%-99.9% of R-diol, or 90%-98% of R-diol, or 90%-99% of R-diol, or 90%-99.5% of R-diol, or 90%-99.9% of R-diol.

The process may be repeated until a racemic mixture of R- and S-diols is obtained and/or until the desired degree of enantiomeric purity of the R- or S-diol is obtained.

According to one embodiment of the invention, the RS-diol of the residue/precipitate is in the form of a free base and/or an acid addition salt; and independently thereof the R- or S-diol of the final solution phase is in the form of a free base and/or an acid addition salt. Accordingly, when the RS-diol comprised in the residue/precipitate is in the form of a free base, then the R- or S-diol comprised in the final solution phase, may be in the form of a free base, an acid addition salt or a mixture of a free base and an acid addition salt. Furthermore, when the RS-diol comprised in the residue/precipitate is in the form of an acid addition salt, then the R- or S-diol comprised in the final solution phase, may be in the form of a free base, an acid addition salt or a mixture of a free base and acid addition salt. Finally, when the RS-diol comprised in the residue/precipitate is a mixture of a free base and an acid addition salt, then the R- or S-diol comprised in the final solution phase, may be in the form of a free base, an acid addition salt or a mixture of a free base and acid addition salt.

The initial non-racemic mixture of R- and S-diol used in the process of the invention may be present as the free base, as salts, or as a mixture of free bases and salts.

Furthermore, the free bases of the diols obtained are optionally converted to acid addition salts thereof or acid addition salts of the diols obtained are optionally converted to other acid addition salts or acid addition salts of the diols obtained are optionally converted to the corresponding free bases by methods known to those skilled in the art.

Precipitation of the RS-diol free base may be carried out by obtaining or dissolving the non-racemic mixture of R- and S-diol free base and/or acid addition salt in a suitable solvent, optionally by applying heat, and then allowing the solution to cool, or by cooling to below ambient temperature. The precipitate is then separated from the mother liquor, preferably by filtration or decanting.

A residue of RS-diol free base may be formed by selective dissolution of R- or S-diol free base and/or acid addition salt into a solvent from the initial non-racemic mixture of R- and S-diols free base and/or acid addition salt in said solvent. The residue is then separated from the organic and/or aqueous phase resulting from the selective dissolution of R- or S-diol.

If the residue/precipitate is crystalline, the crystals are optionally recrystallised one or more times to form racemic diol free base. Then, racemic citalopram free base may be formed from the racemic diol free base by ring closure. The free base of racemic citalopram may optionally be converted to an acid addition salt thereof, preferably the hydrobromide salt.

If the residue/precipitate formed is an oil or an amorphous solid, steps i) and ii) may be repeated until a crystalline product is obtained. The crystals obtained are optionally recrystallised one or more times to form racemic diol free base. Racemic citalopram free base may be formed from the racemic diol free base by ring closure. The free base of racemic citalopram is optionally converted to an acid addition salt thereof, preferably the hydrobromide salt.

The RS-diol free base prepared according to the invention is optionally converted to acid addition salts thereof.

An oily phase separated from the final solution phase is optionally subjected to conventional purification processes.

The RS-diol free base prepared according to the invention may contain a minor excess of the S-diol (or R-diol). It may thus be necessary to repeat steps i) and ii) (in particular crystallisation) of the RS-diol free base one or more times in order to obtain racemic diol. The final solution phases may be pooled together and the diol enantiomer contained herein may be isolated as described below.

Suitable solvents for obtaining the residue/precipitate comprising the RS-diol free base are apolar solvents for example alkanes, such as heptane or hexane, aromatic hydrocarbons such as toluene, benzene and xylene, polar solvents such as acetonitrile, alcohols such as methanol and iso-propylalcohol or ketones such as methyl isobutyl ketone; or mixtures thereof.

In a preferred embodiment, a free base of the RS-diol is obtained in step i), preferably in crystalline form.

If necessary, crystallisation may be initiated by seeding with racemic crystalline diol free base.

The precipitation of RS-diol acid addition salt may be carried out by obtaining or dissolving the non-racemic mixture of R- and S-diol free base or acid addition salt in a suitable solvent, if necessary by applying heat, and adding an acid, for example as a solid, a liquid, in a solution or as a gas.

The acid used for the precipitation of a RS-diol acid addition salt is an acid which precipitates a mixture of R- and S-enantiomers and leaves the mother liquor enriched with either the R- or S-diol enantiomer of the diol as the free base or an acid addition salt.

The acid used for the precipitation of a RS-diol acid addition salt may be:
- added after the initial non-racemic mixture of R- and S-diol free base and/or acid addition salt is obtained or dissolved in a suitable solvent; and/or
- present in the solvent during and/or prior to dissolution of the initial non-racemic mixture of R- and S-diol free base and/or acid addition salt; and/or
- present in the initial non-racemic mixture of R- and S-diol free base and/or acid addition salt during and/or prior to dissolution in the solvent.

A residue of RS-diol acid addition salt may be formed by selective dissolution of R- or S-diol free base and/or acid addition salt into a solvent from the initial non-racemic mixture of R- and S-diols free base and/or acid addition salt in said solvent, if necessary by adding an acid, for example as a solid, a liquid, in a solution or as a gas; or mixtures thereof.

The acidic part of a RS-diol acid addition salt of the residue formed in step i) is an acid, which allows the selective dissolution of either R- or S-diol free base and/or acid addition salt and leaves the undissolved material enriched with the RS-diol acid addition salt.

The acid used for forming the RS-diol acid addition salt of the residue may be:
- present in the solvent before the initial non-racemic mixture of R- and S-diol free base and/or acid addition salt is mixed with the solvent; and/or
- mixed with the solvent together with the initial non-racemic mixture of R- and S-diol free base and/or acid addition salt; and/or
- mixed with the solvent after the initial non-racemic mixture of R- and S-diol free base and/or acid addition salt is mixed with the solvent; and/or
- present in the initial non-racemic mixture of R- and S-diol free base and/or acid addition salt during and/or prior to the mixing with the solvent.

Suitable acids for the formation of a residue/precipitate of RS-diol acid addition salt from an initial non-racemic mixture of R- and S-diol free base and/or acid addition salt are inorganic acids such as hydrochloric acid, hydrobromic acid and sulphuric acid or organic acids such as oxalic acid, p-toluenesulfonic acid, methanesulfonic acid and acetic acid. Hydrobromic acid, hydrochloric acid and oxalic acid are preferred acids. When these acids are used, a hydrobromide salt, hydrochloride salt or oxalate salt of the RS-diol is formed, preferably in crystalline form. Suitably, up to 10 equivalents of acid is used. Accordingly:
- 0.2-10 mol of acid may be used, such as 0.2-0.4 mol, or 0.4-0.6 mol, or 0.9-1.1 mol or 1.8-2.2 mol of acid is used for each mol of S- and R-diol comprised in the initial non-racemic mixture of R- and S-diol free base and/or acid addition salt; and/or
- 0.3-4.0 mol, such as 0.4-0.6 mol, or 0.9-1.1 mol or 1.8-2.2 mol of acid is used for each mol of RS-diol comprised in the residue/precipitate.

In order to increase the ionic strength of the solution, salts such as NaCl may be added to the solution before, during or after the RS-diol acid addition salt is obtained in step i). Those skilled in the art will know how to adjust the amount of salt added to obtain the desired effect.

Suitable solvents for the formation of a residue/precipitate of RS-diol acid addition salt from an initial non-racemic mixture of R- and S-diol free base and/or acid addition salt are polar and apolar solvents such as toluene, ethyl acetate, diethylether, THF, alcohols such as iso-propylalcohol, acetonitrile, and ketones such as acetone and methyl isobutyl ketone, and water.

If the residue/precipitate formed in step i) is crystalline, the crystals are separated from the final solution phase, preferably by filtration or decanting. The crystals are optionally recrystallised by dissolving the crystals in a solvent, preferably by heating, and allowing the solution to cool, or by cooling to below ambient temperature. Racemic citalopram may be formed from the crystalline racemic diol acid addition salt by ring closure. The racemic citalopram may be converted to a pharmaceutically acceptable salt thereof, preferably the HBr salt.

If the residue/precipitate formed in step i) is not crystalline, but amorphous or an oil, or mixtures thereof, steps i) and ii) may be repeated until a crystalline product is obtained. The crystals obtained are optionally recrystallised one or more times as described above. Racemic citalopram may be formed from the crystalline racemic diol acid addition salt by ring closure. The racemic citalopram may be converted into a pharmaceutically acceptable salt thereof, preferably the HBr salt.

An oily phase separated from the final solution phase is optionally subjected to conventional purification processes.

Thus, the RS-diol acid addition salt prepared according to the invention may contain a minor excess of the S-diol (or R-diol). It may thus be necessary to repeat precipitation (in particular crystallisation) of the RS-diol acid addition salt one or more times in order to obtain a racemic mixture. The final solution phase may be pooled together and the diol enantiomer contained herein may be isolated as described below.

If necessary, crystallisation of the RS-diol acid addition salt may be initiated by seeding with the racemic crystalline diol acid addition salt.

The RS-diol acid addition salt prepared according to the invention is optionally converted into other acid addition salts or the corresponding free base.

According to a preferred embodiment of the invention, a free base of the RS-diol or a hydrochloride salt, hydrobromide salt or oxalate salt of the RS-diol is obtained, preferably in crystalline form in steps i), iia) and iib).

The final solution phase, extracts thereof, or a phase enriched with R- or S-diol free base and/or acid addition salt may be subjected to conventional purification processes (such as treatment with active carbon, chromatography etc.) before evaporation of the solvent, and/or it may be subjected to one or more further precipitations of RS-diol free base or RS-diol acid addition salt according to the invention, in order to improve the enantiomeric purity of the diol enantiomer product.

The R- or S-diol free base and/or acid addition salt may be isolated from the final solution phase using conventional procedures such as evaporation of the solvent, or in case the final solution phase is acidic by basification followed by separation of phases or by extraction of R- or S-diol free base and/or acid addition salt followed by evaporation of the solvent.

The final solution phase, extracts thereof, or a phase enriched with R- or S-diol free base and/or acid addition salt may be subjected to conventional purification processes (such as treatment with active carbon, chromatography etc.) before the isolation from the R- or S-diol free base and/or acid addition salts. Suitably, R- or S-diol may be precipitated as a phosphate salt or an oxalate salt by methods known to those skilled in the art.

It has been found that the enantiomeric purity (the ratio between the wanted isomer and the sum of both isomers) of the S- or R-diol free base and/or acid addition salt left in the final solution phase may be as high as 97-98% or even higher (i.e. better) depending on the specific conditions used.

Accordingly, the S-diol (or R-diol) free base and/or acid addition salt prepared according to the invention may contain a minor amount of the R-diol (or S-diol) free base and/or acid addition salt. In one embodiment this minor amount may be less than 3%, or more preferred less than 2%, or most preferred less than 1% (the ratio between the isomer contained in a minor amount and the sum of both isomers).

The R- or S-diol free base and/or acid addition salt may be purified and isolated from said solvent or final solution phase as described above.

In one embodiment, R-diol free base or acid addition salt is obtained.

In another embodiment, S-diol free base or acid addition salt is obtained.

When R- or S-diol free base is obtained, it is optionally converted to acid addition salts thereof. When R- or S-diol acid addition salt is obtained, it is optionally converted to other acid addition salts or to the corresponding free base.

Enantiomerically-pure R- or S-diol free base and/or acid addition salt may be mixed with a non-racemic mixture of R- and S-diol free base and/or acid addition salt to obtain racemic diol free base and/or acid addition salt. Racemic diol free base and/or acid addition salt may then be obtained by one or more precipitations of racemic diol free base and/or an acid addition salt thereof, followed by recrystallisation as described above.

R- or S-citalopram free base and/or acid addition salt may be formed from the corresponding R- or S-diol free base and/or acid addition salt by ring closure with retention of configuration. S-citalopram (or R-citalopram) free base and/or acid addition salt may optionally be converted to an acid addition salt thereof, preferably the oxalate salt and optionally recrystallised.

Ring closure of the R- or S-diol free base and/or acid addition salt may be performed via a labile ester intermediate, e.g. in the presence of tosyl-chloride, in a basic environment, as described in EP-B1-347 066. Then, the ring closing reaction proceeds with retention of the stereochemistry. R- or S-citalopram free base and/or acid addition salt of an enantiomeric purity substantially equal to the starting diol is then obtained.

Ring closure of the obtained racemic diol free base and/or acid addition salt may be performed in an acidic environment, as described in U.S. Pat. No. 4,650,884, or via a labile ester as described above. Thereby, racemic citalopram is obtained.

The thus-obtained enantiomerically-pure R- or S-citalopram free base and/or acid addition salt may be mixed with a non-racemic mixture of R- and S-citalopram free base and/or acid addition salt to obtain racemic citalopram free base and/or acid addition salt. Racemic citalopram free base and/or acid addition salt may then be obtained by one or more precipitations of citalopram free base or an acid addition salt thereof, followed by recrystallisation as described above.

One particular embodiment of the invention relates to a process for the preparation of racemic diol free base or an acid addition salt thereof and/or R- or S-diol as the free base or an acid addition salt thereof by the separation of an initial non-racemic mixture of R- and S-diol with more than 50% of one of the enantiomers into a fraction being enriched with S-diol or R-diol and a fraction consisting of RS-diol wherein the ratio of R-diol:S-diol is equal to 1:1 or closer to 1:1 than in the initial mixture of R- and S-diol wherein i) RS-diol is precipitated from a solvent as the free base or as an acid addition salt thereof;
ii) the precipitate formed is separated from the mother liquor;
   iia) if the precipitate is crystalline it is optionally recrystallised one or more times to form racemic diol;
   iib) if the precipitate is not crystalline, steps i) and ii) are optionally repeated until a crystalline precipitate is obtained and the crystalline precipitate is optionally recrystallised one or more times to form racemic diol;
iii) the mother liquor is optionally subjected to further purification and S-diol or R-diol is isolated from the mother liquor;
iv) the free bases of the diols obtained are optionally converted to acid addition salts thereof or acid addition salts of the diols obtained are optionally converted to other acid addition salts or acid addition salts of the diols obtained are optionally converted to the corresponding free bases.

Another particular embodiment of the invention relates to a process for the preparation of racemic diol free base or an acid addition salt thereof and/or R- or S-diol as the free base or an acid addition salt thereof by the separation of an initial non-racemic mixture of R- and S-diol with more than 50% of one of the enantiomers into a fraction being enriched with S-diol or R-diol and a fraction consisting of RS-diol wherein the ratio of R-diol:S-diol is equal to 1:1 or closer to 1:1 than in the initial mixture of R- and S-diol wherein i) RS-diol is precipitated from a solvent as the free base or as an acid addition salt thereof; or
   R- or S-diol is dissolved into a solvent from the initial non-racemic mixture of R- or S-diols as the free base or as an acid addition salt thereof in said solvent, leaving a residue;
ii) the precipitate formed is separated from the mother liquor;
   iia) if the precipitate is crystalline it is optionally recrystallised one or more times to form racemic diol;
   iib) if the precipitate is not crystalline, steps i) and ii) are optionally repeated until a crystalline precipitate is obtained and the crystalline precipitate is optionally recrystallised one or more times to form racemic diol;
iii) the mother liquor is optionally subjected to further purification and S-diol or R-diol is isolated from the mother liquor;
iv) the free bases of the diols obtained are optionally converted to acid addition salts thereof or acid addition salts of the diols obtained are optionally converted to other acid addition salts or acid addition salts of the diols obtained are optionally converted to the corresponding free bases.

The invention is illustrated by the following examples, which may not be construed as limiting.

EXAMPLES

In the following examples optical purities were measured by Chiral SCFC (super critical fluid chromatography) HPLC.

Example 1

Purification of S-Diol by Precipitation of Racemic Diol as the Hydrochloride Salt General Method:

A mixture of R- and S-diols (as defined in the table below) (10 g) was dissolved in toluene (60 mL). Aqueous hydrochloric acid solution (32 mL, 1 M) was added, and in some cases solid sodium chloride was added (enough so that the concentration of NaCl in the water was approximately 1 M). The mixture was stirred overnight, and filtered. The residue was dried to give crystals of racemic diol hydrochloride, contaminated by some S-diol hydrochloride. The mother liquor was basified with aqueous ammonia solution to pH>9, and the toluene layer was separated. The aqueous layer was washed once more with toluene, and the combined toluene extracts were dried over magnesium sulfate and evaporated under reduced pressure to give mainly S-diol, contaminated with a small amount of R-diol. See table for details. Recovery of material was virtually quantitative, with the expected partitioning of weight between the respective samples.

| Before | | After Precipitation | | | |
|---|---|---|---|---|---|
| Precipitation Mixture of Isomers | | Precipitate (mixture of R and S-diols) | | Oil after basification, separation and evaporation (enriched S-enantiomer) | |
| S % | R % | S % | R % | S % | R % |
| 98.4 | 1.6 | 54 | 46 | 97.9 | 2.1* |
| 95.4 | 4.6 | 55 | 45 | 98.7 | 1.3* |
| 90.3 | 9.7 | 51 | 49 | 96.7 | 3.3 |
| 80 | 20 | 51 | 49 | 96.7 | 3.3 |
| 69 | 31 | 50 | 50 | 94.8 | 5.2 |
| 59 | 41 | 54 | 46 | 92 | 8.0 |

*Denotes that solid NaCl was added to the mixture, sufficient so that the resulting water phase was approximately 1 M in NaCl.

In the following examples optical purity is measured by Chiral HPLC.

Example 2

Purification of S-Diol by Precipitation of Racemic Diol Free Base

A solution of S-diol in acetonitrile (500 mL, ca. 50-55% w/w, S:R ratio 95.72:4.28) at room temperature was cooled with stirring to −14° C. The mixture was seeded with almost-racemic diol (S:R ratio ca. 60:40) after every drop in temperature of 2° C. After 16 hours the mixture was filtered, and the filter cake was dried. Analysis of the filter cake indicated that the S:R ratio was 57.97:42.03. Analysis of the mother liquor indicated that the S:R ratio was 98.065:1.935.

Example 3

Purification of S-Diol by Precipitation of Racemic Diol Free Base

A solution of S-diol in acetonitrile (500 mL, ca. 50-55% w/w, S:R ratio 95.72:4.28) at room temperature was cooled with stirring to −10° C. with cooling at a rate of 1° C./h. The mixture was seeded with almost-racemic diol (S:R ratio ca. 60:40) after every drop in temperature of 5° C. After 40 hours at −10° C. the mixture was filtered, and the filter cake was dried. Analysis of the filter cake indicated that the S:R ratio was 59.19:40.81. Analysis of the mother liquor indicated that the S:R ratio was 98.52:1.48.

Example 4

Purification of S-Diol by Precipitation of Racemic Diol as the Hydrochloride Salt General Method:

A mixture of R- and S-diols (as defined in the table below) (1 g) was dissolved in toluene (10 mL). Aqueous hydrochloric acid solution (1.0 equivalent; concentration as defined in the table below) was added, and solid sodium chloride was added (enough so that the concentration of NaCl in the water was approximately 1 or 2 M; see table below). The mixture was stirred overnight, and filtered. The residue was dried to give crystals of racemic diol hydrochloride, contaminated by some S-diol hydrochloride. The mother liquor was basified with aqueous ammonia solution to pH>9, and the toluene layer was separated. The aqueous layer was washed once more with toluene, and the combined toluene extracts were dried over magnesium sulfate and evaporated under reduced pressure to give mainly S-diol, contaminated with a small amount of R-diol. See table for details. Recovery of material was virtually quantitative, with the expected partitioning of weight between the respective samples.

| Before Precipitation | | | | After Precipitation | | | |
|---|---|---|---|---|---|---|---|
| Mixture of Isomers | | Aqueous HCl | Aqueous NaCl | Precipitate (mixture of R and S-diols) | | Oil after basification, separation and evaporation (enriched S-enantiomer) | |
| S % | R % | Conc. (M) | Conc. (M) | S % | R % | S % | R % |
| 82.3 | 17.7 | 1.0 | 1.0 | 58.4 | 41.6 | 99.4 | 0.6 |
| 82.3 | 17.7 | 2.0 | 1.0 | 49.7 | 50.3 | 97.7 | 2.3 |
| 82.3 | 17.7 | 1.0 | 2.0 | 81.3 | 18.7 | 86.2 | 13.8 |
| 82.3 | 17.7 | 2.0 | 2.0 | 60.1 | 39.9 | 99.7 | 0.3 |

Example 5

Purification of S-Diol by Precipitation of Racemic Diol as P-Toluenesulfonyl, Methanesulfonyl or Acetate Salts General Method:

A mixture of R- and S-diols (as defined in the table below) (1 g) was dissolved in toluene or ether (10 mL; as described in the table below). Aqueous NaCl solution (1 M, 3 mL) was added. The acid (as defined in the table below) was added neat as a liquid. The mixture was stirred overnight, and filtered or decanted. The residue was dried to give an oil or a solid. The mother liquor was basified with aqueous ammonia solution to pH>9, and the toluene or ether layer was separated. The aqueous layer was washed once more with toluene or ether, and the combined organic extracts were dried over magnesium sulfate and evaporated under reduced pressure to give mainly a solid or an oil. See table for details. Recovery of material was virtually quantitative, with the expected partitioning of weight between the respective samples.

| Before Precipitation | | | After Precipitation | | | |
|---|---|---|---|---|---|---|
| | | | Precipitate (mixture of R and S-diols) | | Oil after basification, separation and evaporation (enriched S-enantiomer) | |
| Mixture of Isomers | | | | | | |
| S % | R % | Solvent | Acid (equiv.) | S % | R % | S % | R % |
| 82.3 | 17.7 | Toluene | MsOH (1) | 64.4 | 35.6 | 94.3 | 5.7 |
| 82.3 | 17.7 | Toluene | MsOH (2) | 48.2 | 51.8 | 90.0 | 10.0 |
| 82.3 | 17.7 | Ether | MsOH (1) | 62.9 | 37.1 | 91.0 | 9.0 |
| 82.3 | 17.7 | Ether | MsOH (2) | 55.1 | 44.9 | 89.3 | 10.7 |
| 82.3 | 17.7 | Toluene | AcOH (1) | 71.3 | 28.7 | 96.2 | 3.8 |
| 82.3 | 17.7 | Toluene | AcOH (2) | 65.9 | 34.1 | 94.8 | 5.2 |
| 82.3 | 17.7 | Ether | AcOH (1) | 65.0 | 35.0 | 91.6 | 8.4 |
| 82.3 | 17.7 | Ether | AcOH (2) | 65.7 | 34.3 | 87.2 | 12.8 |

Example 6

Purification of S-Diol by Precipitation of a Racemic Diol Salt in the Absence of Water General Method:

A mixture of R- and S-diols (as defined in the table below) (1 g) was dissolved in toluene or ether (10 mL; as described in the table below). The acid (as defined in the table below) was added neat as a solid. The mixture was stirred overnight, and filtered. The residue was dried to give an oil or a solid. Water was added to the mother liquor, and the mother liquor was basified with aqueous ammonia solution to pH>9, and the toluene or ether layer was separated. The aqueous layer was washed once more with toluene or ether, and the combined organic extracts were dried over magnesium sulfate and evaporated under reduced pressure to give mainly a solid or an oil. See table for details. Recovery of material was virtually quantitative, with the expected partitioning of weight between the respective samples.

| Before Precipitation | | | After Precipitation | | | |
|---|---|---|---|---|---|---|
| | | | Precipitate (mixture of R and S-diols) | | Oil after basification, separation and evaporation (enriched S-enantiomer) | |
| Mixture of Isomers | | | | | | |
| S % | R % | Solvent | Acid (equiv.) | S % | R % | S % | R % |
| 82.3 | 17.7 | Toluene | TsOH (0.4) | 54.9 | 45.1 | 90.9 | 8.1 |
| 82.3 | 17.7 | Ether | TsOH (0.4) | 57.4 | 42.6 | 98.1 | 7.9 |
| 82.3 | 17.7 | Toluene | (CO$_2$H)$_2$ (0.2) | 78.4 | 21.6 | 93 | 7 |
| 82.3 | 17.7 | Toluene | (CO$_2$H)$_2$ (0.4) | 72.1 | 27.8 | 99.97 | 0.03 |
| 82.3 | 17.7 | Toluene | (CO$_2$H)$_2$ (1) | 82.2 | 17.8 | 99.6 | 0.4 |
| 82.3 | 17.7 | Ether | (CO$_2$H)$_2$ (0.2) | 58.0 | 42.0 | 97.7 | 2.3 |
| 82.3 | 17.7 | Ether | (CO$_2$H)$_2$ (0.4) | 55.4 | 44.6 | 98.4 | 1.6 |
| 82.3 | 17.7 | Ether | (CO$_2$H)$_2$ (1) | 72.0 | 28.0 | 99.5 | 0.5 |

Example 7

Purification of S-Diol by Precipitation of a Racemic Diol Salt in the Absence of Water Using Various Solvents General Method:

A mixture of R- and S-diols (as defined in the table below) (1 g) was dissolved in a solvent (10 mL; as described in the table below). The acid (as defined in the table below) was added neat as a solid. The mixture was stirred overnight, and filtered or decanted if a precipitate had formed. Where a precipitate had formed, the residue was dried to give an oil or a solid. The mother liquor was evaporated, and the residue was taken up in a mixture of ether and water. This mixture was basified with aqueous ammonia solution to pH>9, and the ether layer was separated. The aqueous layer was washed once more with ether, and the combined ether extracts were dried over magnesium sulfate and evaporated under reduced pressure to give mainly a solid or an oil. See table for details. Recovery of material was virtually quantitative, with the expected partitioning of weight between the respective samples.

| Before Precipitation | | | After Precipitation | | | |
|---|---|---|---|---|---|---|
| | | | Precipitate (mixture of R and S-diols) | | Oil after basification, separation and evaporation (enriched S-enantiomer) | |
| Mixture of Isomers | | | | | | |
| S % | R % | Solvent | Acid (equiv.) | S % | R % | S % | R % |
| 82.3 | 17.7 | MeOH | TsOH (0.4) | No Precipitation | | | |
| 82.3 | 17.7 | MeOH | (CO$_2$H)$_2$ (0.2) | No Precipitation | | | |
| 82.3 | 17.7 | IPA | TsOH (0.4) | 51.5 | 48.5 | 91.6 | 8.4 |
| 82.3 | 17.7 | IPA | (CO$_2$H)$_2$ (0.2) | 54.9 | 45.1 | 98.3 | 1.7 |
| 82.3 | 17.7 | Acetonitrile | TsOH (0.4) | No Precipitation | | | |
| 82.3 | 17.7 | Acetonitrile | (CO$_2$H)$_2$ (0.2) | 57.2 | 42.8 | 97.2 | 2.8 |
| 82.3 | 17.7 | THF | TsOH (0.4) | No Precipitation | | | |
| 82.3 | 17.7 | THF | (CO$_2$H)$_2$ (0.2) | 53.2 | 46.8 | 98.9 | 1.1 |
| 82.3 | 17.7 | Acetone | TsOH (0.4) | No Precipitation | | | |
| 82.3 | 17.7 | Acetone | (CO$_2$H)$_2$ (0.2) | 56.7 | 43.3 | 98.2 | 1.8 |
| 82.3 | 17.7 | MIBK | TsOH (0.4) | 56.8 | 43.2 | 98.5 | 1.5 |
| 82.3 | 17.7 | MIBK | (CO$_2$H)$_2$ (0.2) | 58.7 | 41.3 | 99.6 | 0.4 |

Example 8

Purification of S-diol by Precipitation of Racemic Diol Oxalate

General Method:

A mixture of R- and S-diols (as defined in the table below) (1 g) was dissolved in toluene (10 mL). An aqueous solution of NaCl was added (1 M, 3 mL) and oxalic acid (as defined in the table below) was added neat as a solid. The mixture was stirred overnight, and filtered or decanted if a precipitate had formed. Where a precipitate had formed, the residue was dried to give an oil or a solid. The mother liquor was basified with aqueous ammonia solution to pH>9, and the toluene layer was separated. The aqueous layer was washed once more with toluene, and the combined toluene extracts were dried over magnesium sulfate and evaporated under reduced pressure to give mainly a solid or an oil. See table for details. Recovery of material was virtually quantitative, with the expected partitioning of weight between the respective samples.

| Before Precipitation | | | After Precipitation | | | |
|---|---|---|---|---|---|---|
| Mixture of Isomers | | Oxalic Acid | Precipitate (mixture of R and S-diols) | | Oil after basification, separation and evaporation (enriched S-enantiomer) | |
| S % | R % | (equiv.) | S % | R % | S % | R % |
| 82.3 | 17.7 | 0.2 | 51.8 | 48.2 | 98.5 | 1.5 |
| 82.3 | 17.7 | 0.4 | 62.6 | 37.4 | 99.8 | 0.2 |
| 82.3 | 17.7 | 1.0 | 58.6 | 41.4 | 97.0 | 3.0 |
| 82.3 | 17.7 | 2.0 | 56.7 | 43.3 | 92.7 | 7.3 |

Example 9

Purification of S-Diol by Precipitation of Racemic Diol Hydrochloride in Water

General Method:

A mixture of R- and S-diols (as defined in the table below) (1 g) was stirred with an aqueous solution of HCl (1 equivalent; see table for concentration). The mixture was stirred overnight, and sufficient NaCl was added (as a solid) so that the concentration of NaCl was 1 M. The mixture was filtered to give a solid. To the mother liquor was added water and ether, was basified with aqueous ammonia solution to pH>9, and the ether layer was separated. The aqueous layer was washed once more with ether, and the combined ether extracts were dried over magnesium sulfate and evaporated under reduced pressure to give mainly a solid or an oil. See table for details. Recovery of material was virtually quantitative, with the expected partitioning of weight between the respective samples.

| Before Precipitation | | | After Precipitation | | | |
|---|---|---|---|---|---|---|
| Mixture of Isomers | | HCl | Precipitate (mixture of R and S-diols) | | Oil after basification, separation and evaporation (enriched S-enantiomer) | |
| S % | R % | conc. (M) | S % | R % | S % | R % |
| 82.3 | 17.7 | 1 | 59.4 | 40.6 | 99.2 | 0.8 |
| 82.3 | 17.7 | 2 | 63.7 | 36.3 | 99.3 | 0.7 |

Example 10

Purification of S-Diol by Preferential Dissolution of S-Diol Hydrochloride in Water General Method:

A mixture of R- and S-diol hydrochloride salts (17.7: 82.3; 5.5 g) was stirred with an aqueous solution of NaCl (1 M, 12 mL). The mixture was stirred overnight, and was filtered to give a solid. To the mother liquor was added water and ether, was basified with aqueous ammonia solution to pH>9, and the ether layer was separated. The aqueous layer was washed once more with ether, and the combined ether extracts were dried over magnesium sulfate and evaporated under reduced pressure to give mainly a solid or an oil. The residue from filtration contained R-diol and S-diol in a ratio of 1.0:99.0. The product from work-up of the filtrate contained R-diol and S-diol in a ratio of 38.8:61.2. Recovery of material was virtually quantitative, with the expected partitioning of weight between the respective samples.

The invention claimed is:

1. A process for the preparation of racemic citalopram diol ("racemic-diol") free base or acid addition salt thereon and/or the corresponding R- or S-diol free base or acid addition salt thereof from an initial non-racemic mixture of R- and S-diol free base or acid addition salt thereof, comprising the steps of:
   i) precipitating a mixture of R- and S-citalopram diol ("RS-diol") in the form of a free base or acid addition salt thereof from a solution of the initial non-racemic mixture, leaving a final solution phase comprising R- or S-diol free base or acid addition salt thereof, wherein the precipitated RS-diol comprises a ratio of R-diol:S-diol that is equal to 1:1 or closer to 1:1 than the initial non-racemic mixture; or mixing a solution of the initial non-racemic mixture with a solvent to preferentially dissolve R- or S-diol free base or acid addition salt thereof into a final solution phase, leaving a residue comprising RS-diol free base or acid addition salt thereof;
   ii) separating the residue/precipitate from the final solution phase;
   iii.a) if the residue/precipitate is crystalline, optionally recrystallizing the residue/precipitate one or more times to form racemic diol; or
   iii.b) if the residue/precipitate is not crystalline, optionally repeating steps i) and ii) until a crystalline residue/precipitate is obtained and optionally recrystallizing the crystalline residue/precipitate one or more times to form racemic diol;
   iv) optionally subjecting the final solution phase to further purification;
   v) isolating S-diol or R-diol free base or acid addition salt thereof from the final solution phase; and
   vi.a) optionally converting the S-diol or R-diol free base to an acid addition salt thereof;
   vi.b) optionally converting the acid addition salt of the S-diol or R-diol free base to another acid addition salt; or
   vi.c) optionally converting the acid addition salt of the S-diol or R-diol free base to the corresponding free base.

2. A process for the preparation of S-citalopram diol or citalopram diol free base or acid addition salt thereof from an initial non-racemic mixture of R- and S-diol free base or acid addition salt thereof, comprising the steps of:
   i) precipitating a mixture of R- and S-citalonram diol ("RS-diol") in the form of a free base or acid addition salt thereof from a solution of the initial non-racemic mixture, leaving a final solution phase, wherein the precipitated RS-diol comprises a ratio of R-diol: S-diol that is equal to 1:1 or closer to 1:1 than the initial non-racemic mixture; or mixing a solution of the initial non-racemic mixture with a solvent to preferentially dissolve R- or S-diol free base or acid addition salt thereof into a final solution phase, leaving a residue comprising RS-diol free base or acid addition salt thereof;
   ii) separating the residue/precipitate from the final solution phase;
   iii) optionally subjecting the final solution phase to further purification; and
   iv) isolating S-diol or R-diol free base or acid addition salt thereof from the final solution phase.

3. The process of claim 2, wherein the diol prepared is the S-diol free base or acid addition salt thereof.

4. The process of claim 2, wherein the diol prepared is the R- diol free base or acid addition salt thereof.

5. A process for the preparation of racemic citalopram diol ("racemic diol") free base or acid addition salt thereof, comprising the steps of:
   i) precipitating a mixture of R- and S-citalopram diol ("RS-diol") in the form of a free base or acid addition salt thereof from a solution of the initial non-racemic mixture, leaving a final solution phase, wherein the precipitated RS-diol comprises a ratio of R- diol: S-diol that is equal to 1:1 or closer to 1:1 than the initial non-racemic mixture; or mixing a solution of the initial non-racemic mixture with a solvent to preferentially dissolve R- or S-diol free base or acid addition salt thereof into a final solution phase, leaving a residue comprising RS-diol free base or acid addition salt thereof;
   ii) separating the residue/precipitate from the final solution phase;
   iiia) if the residue/precipitate is crystalline, optionally recrystallizing the residue/precipitate one or more times to form racemic diol; or
   iiib) if the residue/precipitate is not crystalline, optionally repeating steps i) and ii) until a crystalline residue/precipitate is obtained and optionally recrystallizing the crystalline residue/precipitate one or more times to form racemic diol.

6. The process of claim 1, wherein the initial non-racemic mixture contains more than 50% of S-diol.

7. The process of claim 1, wherein the initial non-racemic mixture contains more than 50% of R-diol.

8. The process of claim 1, wherein the ratio of R-diol:S-diol in the RS-diol of the residue/precipitate is in the range of 0.5:1.5 to 1:1.

9. The process of claim 1, wherein the RS-diol of the residue/precipitate and the R- or S-diol of the final solution phase are each independently in the form of a free base or an acid addition salt thereof.

10. The process of claim 1, wherein RS-diol free base or acid addition salt thereof is precipitated from a solution of the initial non-racemic mixture.

11. The process of claim 1, wherein the RS-diol is precipitated using an acid.

12. The process of claim 11 wherein the initial non-racemic mixture is obtained or dissolved in a suitable solvent and the acid is:
   added after the initial non-racemic mixture is obtained or dissolved in a suitable solvent;
   present in the solvent during and/or prior to dissolution of the initial non-racemic mixture; and/or
   present in the initial non-racemic mixture during and/or prior to dissolution in the solvent.

13. The process of claim 1, wherein a solution of the initial non-racemic mixture is mixed with a solvent to preferentially dissolve R- or S-diol free base or acid addition salt thereof into a final solution phase, leaving a residue comprising RS-diol free base or acid addition salt thereof.

14. The process of claim 1, wherein RS-diol acid addition salt is formed as a residue having an acidic part that comprises an acid.

15. The process of claim 13 wherein the acid is:
   present in the solvent before the initial non-racemic mixture is mixed with the solvent;
   mixed with the solvent together with the initial non-racemic mixture;
   mixed with the solvent after the initial non-racemic mixture is mixed with the solvent; and/or
   present in the initial non-racemic mixture during and/or prior to the mixing with the solvent.

16. The process of claim 14, wherein the initial non-racemic mixture is mixed with a solvent selected from toluene, ethylacetate, diethylether, THF, water, alcohols, acetonitrile, ketones, and mixtures thereof.

17. The process of claim 1, wherein the residue/precipitate is formed using an acid selected from HCl, HBr, $H_2SO_4$, p-toluenesulfonic acid, methanesulfonic acid, acetic acid, and oxalic acid.

18. The process of claim 17, wherein the acid is selected from HCl, HBr, and oxalic acid.

19. The process of claim 1, wherein the residue/precipitate is formed using 0.2-10 mol of acid for each mol of S- and R-diol comprised in the initial non-racemic mixture.

20. The process of claim 1, wherein the residue/precipitate is formed using 0.3-4.0 mol of acid for each mol of RS-diol comprised in the residue/precipitate.

21. The process of claim 1, wherein the residue/precipitate is RS-diol free base in crystalline form.

22. The process of claim 1, wherein the residue/precipitate is RS-diol free base and the initial non-racemic mixture is in a solvent selected from alkanes, aromatic hydrocarbons, polar solvents, alcohols, ketones, and mixtures thereof.

23. The process of claim 1, wherein the final solution phase is subjected to one or more further purifications according to steps i) and ii) before isolation of the S-diol or R-diol free base or acid addition salt thereof from the final solution phase.

24. The process of claim 1, wherein the S-diol or R-diol free base or acid addition salt thereof is isolated from the final solution phase by evaporation of the solvent.

25. The process of claim 1, wherein the final solution phase is acidic and the S-diol or R-diol free base or acid addition salt thereof is isolated from the final solution phase by basification of the final solution phase, followed by phase separation or extraction with a solvent, followed by evaporation of the solvent.

26. The process of claim 1, wherein the S-diol or R-diol free base or acid addition salt thereof is isolated from the final solution phase by precipitation of the R- or S-diol free base or acid addition salt thereof.

27. The process of claim 1, wherein the S-diol or R-diol free base or acid addition salt thereof obtained contains a minor amount of the opposite enantiomer.

28. A method for the preparation of citalopram free base or an acid addition salt thereof, and/or S-citalopram free base or an acid addition salt thereof or R- citalopram free base or an acid addition salt thereof, comprising the process of claim 1 followed by ring closure.

29. The process of claim 6, wherein the initial non-racemic mixture contains more than 70% of S-diol.

30. The process of claim 29, wherein the initial non-racemic mixture contains more than 90% of S-diol.

31. The process of claim 7, wherein the initial non-racemic mixture contains more than 70% of R-diol.

32. The process of claim 31, wherein the initial non-racemic mixture contains more than 90% of R-diol.

33. The process of claim 8, wherein the ratio of R-diol:S-diol in the RS-diol of the residue/precipitate is 0.5:1.5, 0.9:1.1, 0.95:1.05, 0.99:1.01, 0.98:1.02, or 1:1.

34. The process of claim 16, wherein the solvent is selected from iso-propylalcohol, acetone, methyl isobutyl ketone, and mixtures thereof.

35. The process of claim 18, wherein a crystalline hydrobromide salt, hydrochloride salt or oxalate salt of the RS-diol is formed.

36. The process of claim 19, wherein the residue/precipitate is formed using an amount of acid selected from 0.2-0.4 mol, 0.4-0.6 mol, 0.9-1.1 mol, and 1.8-2.2 mol, for each mol of S- and R-diol comprised in the initial non-racemic mixture.

37. The process of claim 20, wherein the residue/precipitate is formed using an amount of acid selected from 0.4-0.6 mol, 0.9-1.1 mol, and 1.8-2.2 mol for each mol of RS-diol comprised in the residue/precipitate.

38. The process of claim 22, wherein the solvent is selected from heptane, hexane, toluene, benzene, xylene, acetonitrile, methanol, iso-propylalcohol, methyl isobutyl ketone, and mixtures thereof.

39. The process of claim 26, wherein an S-diol or R-diol acid addition salt is precipitated in the form of a phosphate salt or an oxalate salt.

40. The process of claim 27, wherein the S-diol or R-diol free base or acid addition salt thereof obtained contains less than 3% of the opposite enantiomer.

41. The process of claim 40, wherein the S-diol or R-diol free base or acid addition salt thereof obtained contains less than 2% of the opposite enantiomer.

42. The process of claim 41, wherein the S-diol or R-diol free base or acid addition salt thereof obtained contains less than 1% of the opposite enantiomer.

* * * * *